United States Patent
Kupferschmid

(10) Patent No.: US 10,473,144 B2
(45) Date of Patent: Nov. 12, 2019

(54) BENT TUBULAR SHAFT AND METHOD FOR PRODUCING THE SAME

(71) Applicant: AESCULAP AG, Tuttlingen (DE)

(72) Inventor: Bernhard Kupferschmid, Emmingen-Liptingen (DE)

(73) Assignee: Aesculap AG (DE)

( * ) Notice: Subject to any disclaimer, the term of this patent is extended or adjusted under 35 U.S.C. 154(b) by 0 days.

(21) Appl. No.: 14/275,498

(22) Filed: May 12, 2014

(65) Prior Publication Data

US 2014/0331812 A1    Nov. 13, 2014

(30) Foreign Application Priority Data

May 13, 2013   (DE) .................. 10 2013 208 729

(51) Int. Cl.
| | |
|---|---|
| *F16C 1/20* | (2006.01) |
| *B21K 1/06* | (2006.01) |
| *A61B 17/29* | (2006.01) |
| *F16C 1/00* | (2006.01) |
| *A61B 17/00* | (2006.01) |

(52) U.S. Cl.
CPC ............ *F16C 1/205* (2013.01); *B21K 1/06* (2013.01); *Y10T 29/49908* (2015.01); *Y10T 74/20456* (2015.01)

(58) Field of Classification Search
CPC .... A61B 2017/2901; A61B 2017/2902; A61B 2017/2904; A61B 2017/2905; A61B 2017/2908; F16C 1/10; F16C 1/20; F16C 1/205; F16C 1/00; Y10T 29/49908; B21D 7/00; B21D 7/0222; B21D 7/10; B21K 1/063
See application file for complete search history.

(56) References Cited

U.S. PATENT DOCUMENTS

| | | | | |
|---|---|---|---|---|
| 2,171,907 A | * | 9/1939 | Beehler | B21D 7/024 72/154 |
| 3,685,335 A | * | 8/1972 | Kowal | B21D 7/022 72/217 |
| 4,292,834 A | * | 10/1981 | Tishler | B21D 11/10 140/92.1 |
| 5,286,253 A | | 2/1994 | Fucci | |

(Continued)

FOREIGN PATENT DOCUMENTS

| | | |
|---|---|---|
| DE | 195 20 717 A1 | 12/1996 |
| DE | 69319199 T2 | 10/1998 |

(Continued)

*Primary Examiner* — Christopher M Koehler
(74) *Attorney, Agent, or Firm* — RatnerPrestia

(57) ABSTRACT

The disclosed embodiments describe a method for producing a bent tubular shaft for a tubular shaft instrument as well as a tubular shaft produced in such manner as well as a tubular shaft instrument with such a bent tubular shaft. The tubular shaft is produced by providing a hollow shaft component and an actuating rod. The actuating rod in this case has at least one bending area in which flexible segments and support segments alternate. The at least one bending area of the actuating rod is provided with a friction-reducing layer before it is inserted into the shaft component in order to create a tubular shaft. The tubular shaft is then bent in an area that corresponds to the at least one bending area of the actuating rod.

4 Claims, 2 Drawing Sheets

(56) References Cited

U.S. PATENT DOCUMENTS

| | | | | |
|---|---|---|---|---|
| 5,615,572 | A * | 4/1997 | Johnson | B21D 7/066 72/389.1 |
| 5,833,692 | A * | 11/1998 | Cesarini | A61B 17/32002 606/170 |
| 5,922,003 | A * | 7/1999 | Anctil | A61B 17/32002 156/293 |
| 6,883,360 | B2 * | 4/2005 | Bates | B21D 7/022 72/159 |
| 7,743,636 | B2 * | 6/2010 | Rusch | B21D 7/02 72/149 |
| 2003/0028207 | A1 * | 2/2003 | Lang | A61B 17/1611 606/167 |
| 2005/0177168 | A1 * | 8/2005 | Brunnett | A61B 17/1624 606/80 |
| 2008/0071303 | A1 * | 3/2008 | Hacker | A61B 17/32002 606/180 |
| 2010/0024515 | A1 * | 2/2010 | Hough | B21D 7/00 72/458 |
| 2010/0234687 | A1 * | 9/2010 | Azarbarzin | A61B 17/29 600/201 |
| 2010/0268254 | A1 | 10/2010 | Golden et al. | |
| 2011/0079627 | A1 * | 4/2011 | Cardinale | A61B 17/0642 227/176.1 |
| 2011/0230867 | A1 | 9/2011 | Hirschfeld et al. | |
| 2011/0245812 | A1 * | 10/2011 | Blocher | A61B 17/06109 606/1 |
| 2011/0276083 | A1 | 11/2011 | Shelton, IV et al. | |
| 2014/0114293 | A1 * | 4/2014 | Jeong | A61B 19/22 606/1 |

FOREIGN PATENT DOCUMENTS

| | | |
|---|---|---|
| DE | 102010011926 A1 | 9/2011 |
| EP | 0 577 423 A2 | 1/1994 |

* cited by examiner

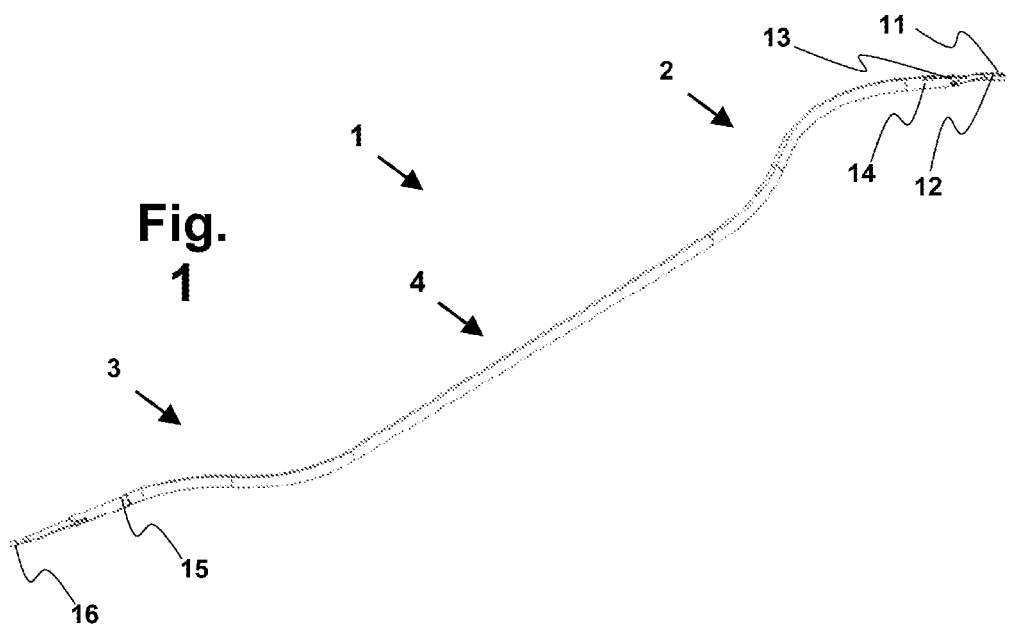
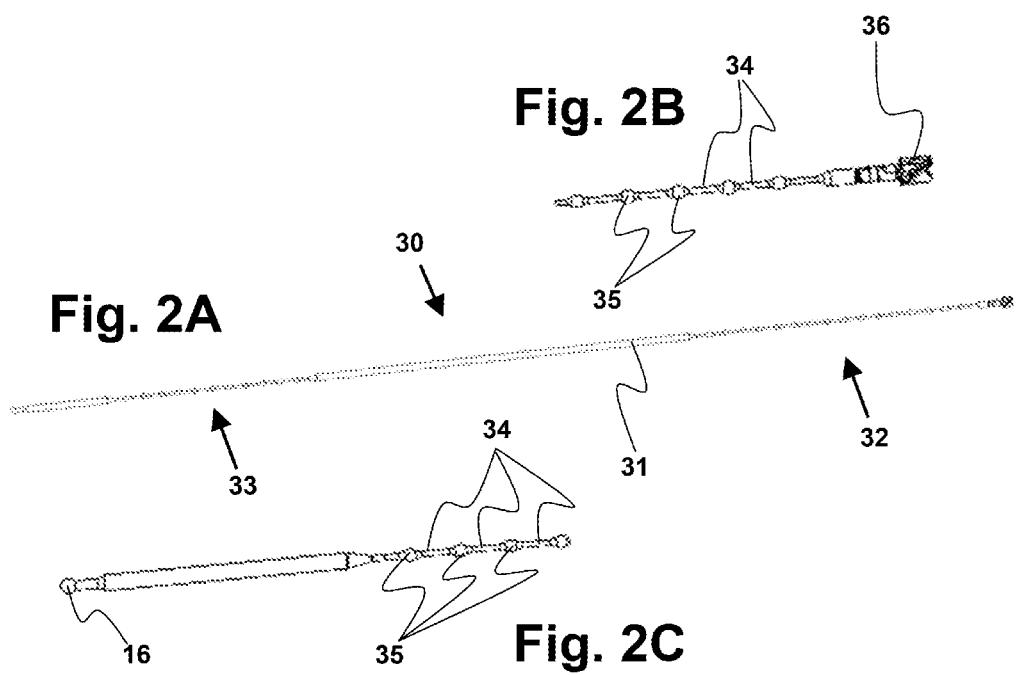

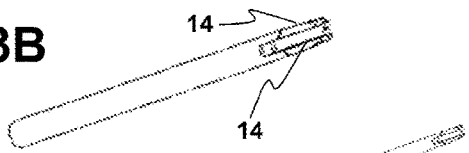
Fig. 3B
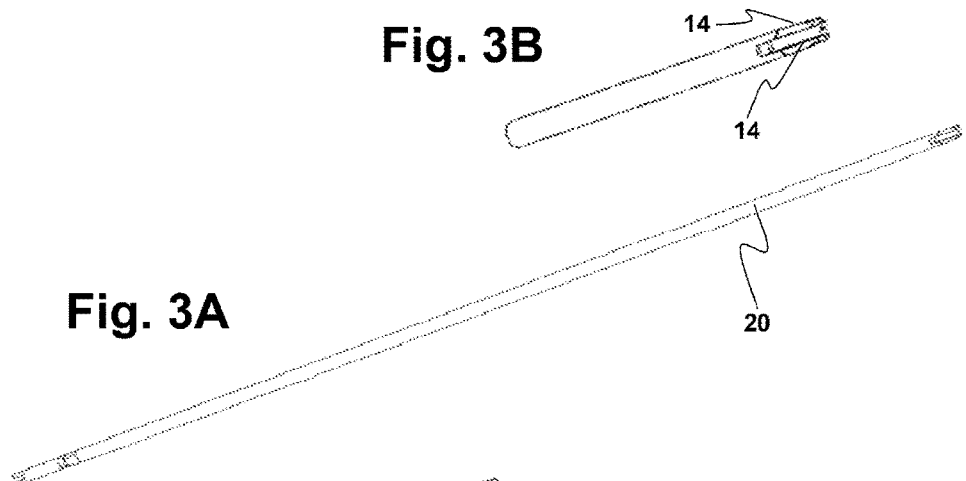
Fig. 3A
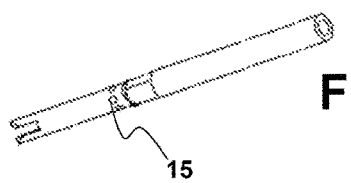
Fig. 3C
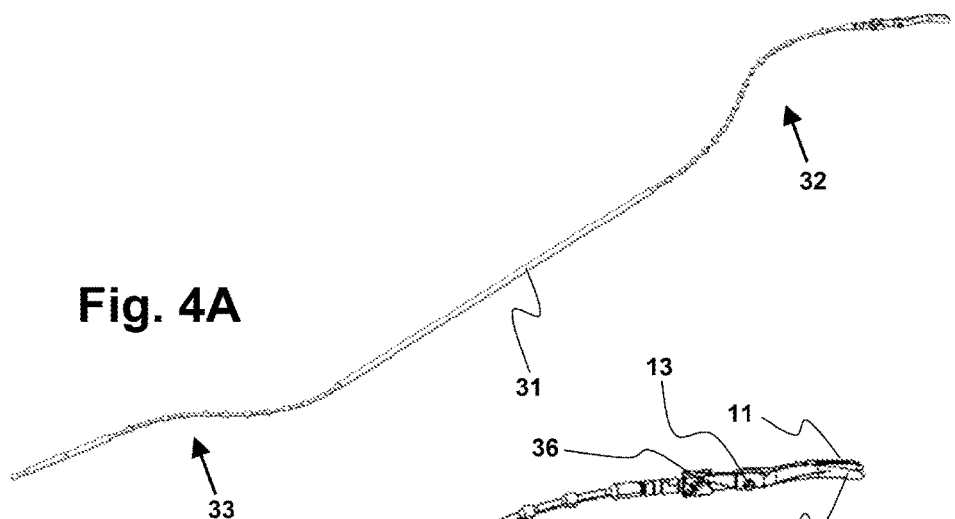
Fig. 4A
Fig. 4B

BENT TUBULAR SHAFT AND METHOD FOR PRODUCING THE SAME

This application claims the priority benefit under 35 U.S.C. § 119 to German Patent Application DE102013208729.2 filed on May 13, 2013, which is hereby incorporated in its entirety by reference.

FIELD OF THE INVENTION

The disclosed embodiments relate to a bent tubular shaft or a tubular shaft instrument as well as a process for producing the same as well as a tubular shaft instrument with a bent tubular shaft of this type.

BACKGROUND

Numerous tubular shaft instruments and thus also numerous tubular shafts are known from the related art. For example, European patent application EP 0577 423 A2 discloses a classic tubular shaft instrument in which a push and pull rod can be moved back and forth axially in its own shaft to allow the jaw part of the tubular shaft instrument to open and close. In this process, the back-and-forth movement of the push and pull rod is transmitted to the halves of the jaw part via a joint mechanism. The push and pull rod can be constructed as a rigid rod. This principle does not facilitate the production of bent tubular shafts.

Tubular shaft instruments with bent tubular shaft are also already known from the related art. For example, the German patent application DE 195 20 717 A1 discloses a tubular shaft instrument having a bent tubular shaft. This tubular shaft instrument employs a shaft having a straight proximal area and bent distal area. In the straight proximal area a rigid rod is used as push and pull rod, to the distal end of which a flexible push and pull rod is attached. The flexible push and pull rod is comprised of a rod in which a plurality of circumferential groves is incorporated, which reduces the cross-section of the rod such that the originally essentially rigid rod becomes flexible. Segments are left between the grooves where the push and pull rod retains its original diameter. These segments enable the push and pull rod to be correctly guided and supported in the bent section of the shaft. The push and pull rod tends in the bent shaft segment to assume not the intended shape of an arc, as it is prescribed by the bent area of the shaft, but rather the shape of a polygonal curve. In this context the number and spacing of support segments determines the shape of the polygonal curve. However, a tubular shaft constructed in this manner can be provided only with a single bend area.

If multiple bent areas are supposed to be provided on a tubular shaft instrument that are to be connected, for example, by straight sections, the entire push and pressure rod must be formed with grooves and support segments, because such type of tubular shaft cannot otherwise be assembled. The straight rigid sections then cannot be pushed through the bends in the shaft. However, if a push and pull rod that is equipped with grooves and support segments over the entire length is used, the inner friction of the tubular shaft is increased greatly. This is because a push rod soft enough to bend tends to deviate laterally and to press against the shaft from inside, which leads to additional friction. With a straight rigid rod, this virtually never happens. Additionally, with a push and pull rod that is flexible throughout its entire length, the play between the actuation unit on the proximal end of the tubular shaft and the functional unit on the distal end of the tubular shaft increases, which compromises the operation of the instrument.

SUMMARY OF THE INVENTION

One aspect of the disclosed subject matter provides a tubular shaft which can have a plurality of bent sections without causing excessive inner friction in the tubular shaft. A further aspect of the disclosed subject matter seeks to provide a bent tubular shaft having minimal play. Yet another aspect of the disclosed subject matter seeks to provide a process for producing such a tubular shaft as well as a tubular shaft instrument with a bent tubular shaft of the type specified.

These aspects are achieved through a process for producing a bent tubular shaft according to claim 1, a tubular shaft according to claim 8, and a tubular shaft instrument according to claim 14. Advantageous embodiments of the disclosed subject matter are the subject matter of the dependent claims.

According to an aspect of the disclosed subject matter, a process for producing a bent tubular shaft for a tubular shaft instrument is disclosed having the following steps. Initially, a hollow shaft component is provided, after which an actuating rod is provided, the actuating rod having at least one bending area in which flexible segments and support segments alternate. Subsequently, at least one bending area of the actuating rod is equipped with a friction-reducing layer. Afterwards, the actuating rod is placed into the hollow shaft component in order to create a tubular shaft, and the tubular shaft is bent in one area that corresponds to at least one bending area of the actuating rod. According to this production process, the production of a tubular shaft instrument with a nonlinear shaft can be simplified significantly and the tubular shaft thus exhibits improved functional capability.

If individual parts of the tubular shaft are already produced in nonlinear form, the assembly is very complicated. In this case, the pull or push element in the interior of the tubular shaft must be bendable over its entire length so that it can be inserted into the shaft component. If the actuating element is formed as a push element, this means that the push element attempts to deviate laterally over its entire length during actuation of the same, which leads to increased friction between the push element and the shaft component, which reduces the service life of the tubular shaft and also reduces the accuracy during operation. If the actuating element is formed as a pull element, this means, on one hand, that the connection to the pull element results in a very small diameter of the pull element in this area, which, in turn, means that only very limited forces can be transferred. At the same time, the pull element rubs on the inside of the tubular shaft when there is tensile load in the bending area over a relatively large length, which, in turn, increases the required actuating forces, but reduces the accuracy of operation and the service life of the instrument and/or the tubular shaft. The actuating rod of the disclosed embodiments, which constitutes the actuating element of the tubular shaft and can be used both as a pull element and preferably as a pressure element, has, in contrast, significant advantages. Because the tubular shaft is not bent until after the actuating rod is inserted, said tubular shaft can have large areas in which it is essentially rigid, at least in relation to the forces occurring in practice. In this area, there is no lateral deviation during tensile loading in terms of lateral buckling, which means that only minimal friction prevails between the actuating rod and the tubular shaft inner wall over this length. In the bending area, the support segments ensure that only a small contact surface can form between the actuating rod and the tubular shaft and that the friction is also significantly less in this area than it is with a conventional tubular shaft. If the actuating rod is being used as a pull element, the support segments also ensure that the center axis of the actuating rod almost never deviates from the center axis of the tubular shaft, which leads to improved accuracy when operating the tubular shaft. Furthermore, this also makes the production process for the tubular shaft less expensive.

According to an advantageous embodiment of an aspect of the disclosed subject matter, at least one functional element is placed at the distal end of the hollow shaft component or of the actuating rod before the tubular shaft is bent; preferably a functional element is placed, in each case, at the distal ends of the shaft component and the actuating rod.

It is advantageous to place the functional elements at the actuating rod and the shaft component before the tubular shaft is bent, because the actuating rod and the shaft component then no longer have to be secured separately from moving against one another for the bending, since this can be handled by the functional elements.

According to a further advantageous embodiment of an aspect of the disclosed subject matter, the step of providing the at least one bending area of the actuating rod with a friction-reducing layer includes pulling shrink tubing over the at least one bending area of the actuating rod and shrinking the shrink tubing at the at least one bending area of the actuating rod.

The friction-reducing layer has two tasks. The first task is to reduce the friction between actuating rod and the shaft component. This goal is achieved by using material for this layer having a lower friction coefficient when interacting with the shaft component than the material of the actuating rod. Typically, the actuating rod is produced from a metal. Alternatively, the actuating rod may be produced from a plastic, and the friction-reducing layer is then directly formed by the surface of the actuating rod. The second task of the friction-reducing layer is to compensate for the deformations that result in the bending area from the bending of the originally circular cross-sections. When a circular tube is bent, the tube cross-section deforms in the bending area, essentially forming an elliptical shape. Not providing play or a compensating layer for these deformations would render the tubular shaft barely, if at all, usable after being bent. If a gap is provided as play between the actuating rod and the shaft component, this will negatively affect accuracy when the tubular shaft is actuated. For this reason, the use of a compensating layer is especially advantageous. Conventional shrink tubes have proven to be especially suitable for reducing the friction between the shaft component and the actuating rod. Furthermore, these tubes are also very good as a compensating layer, because they are sufficiently soft enough to be pressed together at the required points between the shaft component and the actuating rod—particularly its support segments—without causing excessive friction between the contacting components. Furthermore, conventional shrink tubes are particularly easy to attach to the actuating rod and comparatively economical to produce and procure. Alternatively, a friction-reducing layer can also be applied as a coating to the actuating rod or the interior wall of the shaft component. This type of coating can also assume the function of a compensating layer.

According to another advantageous embodiment of an aspect of the disclosed subject matter, the tubular shaft for the step of bending the tubular shaft is grasped in areas that are located outside of the at least one bending area of the actuating rod. This reduces the risk that the tubular shaft would be damaged during bending. In the areas outside of the at least one bending area, the actuating rod has a cylindrical shape. In the bending areas on the other hand, the outer diameter of the actuating rod is variable. If the tubular shaft, for example, is grasped by machine in a bending area and a small amount of excessive force is applied, it is possible for a part of the shaft component to be pushed into the area between two adjacent support segments of the bending area. This will make the tubular shaft unusable. If a little too much force is applied to the shaft component in an area in which the actuating rod is cylindrical to the extent that a part of the shaft component is pushed inward, this might increase the friction between the actuating rod and the shaft component, but it will not cause jamming and the tubular shaft will not necessarily be unusable.

According to yet another advantageous embodiment of an aspect of the disclosed subject matter, the at least one bending area of the actuating rod is produced in that flexible segments are formed on a cylindrical rod by removing material from the rod and support elements are formed in that the original diameter of the cylindrical rod is essentially retained in at least one transverse direction at these sections. This means that the actuating rod, for example, can be formed from a cylindrical rod, for example from a titanium alloy. The at least one bending area in this case can be machined in a lathe process or an EDM (electrical discharge machining) process such as, for example, spark machining (wire EDM, sinker EDM). Alternatively, the actuating rod may also be cast or injection molded, for example from a solid plastic or a composite material. As another alternative, a flexible elastic rod may be used on which the support segments are injection molded, bonded, clamped, or attached in some other manner. The support segments in this case may be made of a material different than that of the flexible elastic rod. In the areas outside of the bending area, a rigid sleeve, for example, may be attached to the flexible rod, or the actuating rod is composed of various components in its longitudinal direction.

According to another advantageous embodiment of an aspect of the disclosed subject matter, the flexible segments are formed as cylindrical sections having a smaller cross-sectional area than the rod outside the at least one bending area and the support segments being essentially spherical and having a maximum diameter that essentially corresponds to the diameter of the cylindrical rod outside the at least one bending area, with two adjacent support segments being preferably connected by a flexible section. This represents a form of the actuating rod that is easy to produce and suitable. The support segments may, however, also have a shape that is not of circular or spherical symmetry and then be rotated in their position along the longitudinal direction of the actuating rod such that the support is uniform in all transverse directions.

According to yet another advantageous embodiment of an aspect of the disclosed subject matter, the at least one bending area of the actuating rod does not extend up to one of its two axial ends. In this case the insertion of the bending rod into the shaft component can only take place in the unbent, i.e. linear, condition, because otherwise the rigid area would become wedged at the end of the actuating rod in the already bent shaft component.

According to a another aspect of the disclosed subject matter, a tubular shaft for a tubular shaft instrument is disclosed with a hollow shaft component, an actuating rod arranged in the hollow shaft component, and functional elements that are attached at the distal ends of the shaft component and/or of the actuating rod, the actuating rod being movable relative to the hollow shaft component in the axial direction in order to thereby move the distal sections of the functional elements toward one another, past one another, and/or away from one another. The actuating rod has, in addition, at least one bending area in which flexible segments and support segments alternate and in which the actuating rod has significantly less bending resistance than outside the at least one bending area. In addition, a friction-reducing layer is provided on the at least one bending area of the actuating rod, which reduces the friction of the actuating rod on the inside wall of the shaft component.

With a tubular shaft having this construction, it is possible to assemble the tubular shaft in linear and/or unbent form and to subsequently bend it into the desired shape. Furthermore, the assembly of the actuating rod and the shaft component is greatly simplified as compared to a tubular shaft with which the components are assembled in the already bent shape. The term "bent components" within the scope of this application not only refers to components that have been bent from some sort of starting shape into a different shape but also components that have been produced in a shape that has at least one area that follows the shape of a bend.

According to an advantageous embodiment of an aspect of the disclosed subject matter, the material of the friction-reducing layer has a lower elasticity module than the material of the actuating rod. In this manner, the friction-reducing layer can also serve as the compensating layer for the previously described deformations of the components during the bending process of the tubular shaft.

According to a further advantageous embodiment of an embodiment of the disclosed subject matter, the actuating rod, with its at least one bending area, is formed as a single piece. The actuating rod, with its at least one bending area with a changeable cross-section, may be produced, for example, through turning on a lathe (machining) or an EDM process. However, it can also be injection molded, for example. The actuating rod may be produced from metal, plastic, or another composite material. Alternatively, the actuating rod may also consist of or include a plurality of components, for example a cylindrical flexible rod and the support segments attached to this and at least one rigid sleeve for stiffening the actuating rod outside of the bending areas.

According to yet another advantageous embodiment of an aspect of the disclosed subject matter, a plurality of bending areas is formed on the actuating rod, with an area being provided between two adjacent bending areas at which the actuating rod is essentially rigid. In this manner, a tubular shaft can be produced, for example, which has a bending area in the area of its two ends but is linear in between. The rigid area of the actuating rod in this case ensures minimal friction between the actuating rod and/or the friction-reducing layer and the shaft sleeve.

According to a further advantageous embodiment of an aspect of the disclosed subject matter, the hollow shaft component has a slotted area on its distal end, in which a slot spaces or separates two bars from one another, and the functional elements each have at least one passage hole through which an axle extends, which is fastened to the bars on both sides of the functional elements. While the functional elements may each be arranged on their own rotational axle, it is advantageous, however, if all of the functional elements are arranged on one axle. The at least one axle is attached to the two bars at the one end of the shaft component. This ensures easy assembly of the tubular shaft.

According to yet another advantageous embodiment of an aspect of the disclosed subject matter, the functional elements are connected to the actuating rod via a sliding component, and at least one functional element preferably has at least one cam that detachably protrudes into the at least one guide track, which is provided in the sliding component, the cam further preferably extending perpendicularly with respect to the axial direction of the tubular shaft. With a sliding component and corresponding guide tracks and cams that glide along them, the pattern of an opening and closing movement of the functional parts can be adjusted. Thus, it is possible, for example, to achieve a great distance with only a small stroke of the actuating rod at the start of a closing process, for example of a clip applicator, while only a small distance is traveled at the end of this closing process with the same stroke of the actuating rod, but a great amount of pressing force is delivered for the clip.

According to another aspect of the disclosed subject matter, a tubular shaft instrument is disclosed with a previously described tubular shaft that was produced according to a likewise previously described process.

Additional advantages and features of the disclosed subject matter are obvious to the person skilled in the art from the attached figures and the detailed description of the exemplary embodiments.

BRIEF DESCRIPTION OF THE DRAWINGS

FIG. 1 shows an isometric view of a tubular shaft according to an exemplary embodiment;

FIGS. 2A-C show isometric views of an actuating rod of a tubular shaft according to the exemplary embodiment in FIG. 1 in the unbent condition;

FIGS. 3A-C show isometric views of a shaft sleeve of a tubular shaft according to the exemplary embodiment in FIG. 1 in the unbent condition; and FIGS. 4A-B show isometric views of an actuating rod of a tubular shaft according to the exemplary embodiment in FIG. 1 in the bent condition.

DETAILED DESCRIPTION OF THE DISCLOSED EMBODIMENTS

An exemplary embodiment of the disclosed subject matter is described in detail in the following with reference being made to the figures.

A tubular shaft 1 according to this exemplary embodiment has two bent areas or bending areas, 2 and 3, as well as a straight area 4. At the distal end of the tubular shaft 1 are functional parts 11, 12, which are rotatably attached by an axle 13 at the bars 14, which are formed at the distal end of the shaft component 20. In this exemplary embodiment, the functional parts 11, 12 together form shears. At the proximal end of the tubular shaft 1, a coupling is formed with which the tubular shaft may be detachably mounted onto the handle component. The tubular shaft 1 with this exemplary embodiment is designed as a disposable article that can be mounted onto a reusable handle part (not shown). The shaft sleeve 20 has ball adapters 15 for coupling, into which the balls insert as securing elements in order to retain the shaft sleeve 20 on the handle part. The actuating rod 30 has a coupling ball 16 on its proximal end that may be detachably coupled to a corresponding adapter on the handle part in order to transfer an actuation of the actuating element of the handle part to the actuating rod 30 and thus ensure function of the functional parts 14.

In the bending areas 32, 33 of the actuating rod 30, flexible segments 34 and support segments 35 alternate, and the actuating rod 30 has significantly lower bending resistance than in the straight area 31 outside of the two bending areas 32, 33. In this exemplary embodiment the bending areas 32, 33 have the approximate appearance of a string of pearls. A shrink tube (not shown in the figures) is arranged at the two bending areas 32, 33 of the actuating rod 30 as a friction-reducing layer. The shrink tube pieces also serve as a compensating layer for deformations that result during the bending process of the tubular shaft 1 at the actuating rod 30 but also particularly at the shaft sleeve 20. The shrink tube is made of plastic and has a lower elasticity modulus than the actuating rod 30 and the shaft sleeve 20, which are produced from a titanium alloy.

The actuating rod 30, i.e. the bending areas 32, 33 of the same, is/are milled from a cylindrical rod and are therefore formed as a single piece. In the straight area 31, the actuating rod 30 is essentially to be considered rigid with respect to the forces occurring during the bending process and proper use. At the distal end of the actuating rod 30, a sliding component 36 is provided having two guide tracks with a cam protruding into each that is provided on the proximal end of each functional elements 11, 12 and inserts into the slide element. Advantageously, the sliding component 36 is axially rotatable in relation to the actuating rod 30 not only in this exemplary embodiment, which means that during insertion of the actuating rod 30 into the shaft sleeve 20, attention does not have to be paid to the alignment of the actuating rod 30.

For the assembly of the tubular shaft 1 according to this exemplary embodiment, two pieces of shrink tubing (not shown) are pushed over the two bending areas 32, 33 of the actuating rod 30 and shrunk through heating. The proximal end of the actuating rod 30 is then inserted into the opening on the distal end of the shaft sleeve 20 and pushed into the shaft sleeve 20 until only the sliding element 36 is protruding at the front (distally) from the shaft sleeve 20. The cams of the functional parts 11, 12 are then threaded into the guide tracks, and the actuating rod 30 is then pushed a bit further into the shaft sleeve 20 until the bearing holes of the functional parts align with the bearing holes in the bars 14 of the shaft component. A bearing axle is then pushed through the bearing holes of the bars 14 and the functional parts 11, 12 and affixed to the bars 14. Finally, the tubular shaft 1 assembled in this manner is bent at the points at which the bending areas 32, 33 of the actuating rod 30 are arranged on the interior of the shaft sleeve 20 and the tubular shaft 1 is placed into the desired shape in this manner.

According to further exemplary embodiments of the disclosed subject matter, the friction-reducing layer may also consist of or include a coating, put-on half shells or partial shells and/or an injection molded material. The friction-reducing layer may either be provided only at the bending areas 32, 33 or over the entire length of the actuating rod 30. It is also possible for the friction-reducing layer to be provided at the bending areas 32, 33 only at the spacers, since the flexible segments do not come into contact with the shaft sleeve and compensation of the deformations at the flexible segments is not required.

The bending areas may also be formed in a different manner. The uniform string-of-pearls shape previously shown can be modified to the extent that the support segments have different spacing with respect to one another, that the flexible segments have different cross-sectional areas and/or shapes and/or are arranged outside the longitudinal direction of the actuating rod.

If more than one bending area is provided in an exemplary embodiment, the bends in each bending area may lie in one and the same plane. As an alternative to this, the planes in which the bending in the individual bending areas takes place may be skewed with respect to one another. As another alternative, it is also possible for a bending area to be simultaneously bent in multiple spatial directions such that the tubular shaft, for example, takes on a spiral shape in this section.

A person skilled in the art may furthermore combine the described features of the tubular shaft in any suitable manner.

The invention claimed is:

1. A method for producing a bent tubular shaft for a tubular shaft instrument comprising:
   providing a hollow shaft component,
   providing an actuating rod, wherein the actuating rod has at least one bending area in which flexible segments and support segments alternate,
   providing the at least one bending area of the actuating rod with a friction-reducing layer, inserting the actuating rod into the hollow shaft component in order to create a tubular shaft, and
   bending of the tubular shaft in an area that corresponds to the at least one bending area of the actuating rod, including grasping the tubular shaft in an area located outside the at least one bending area of the actuating rod,
   wherein the at least one bending area of the actuating rod is produced, in which flexible segments are formed on a cylindrical rod by removing material from the rod, and support elements are formed, in which the original diameter of the cylindrical rod is essentially retained in at least one transverse direction at these sections, and
   wherein the flexible segments are formed as cylindrical sections having a smaller cross-sectional area than the rod outside the at least one bending area, and wherein the support segments are formed essentially spherical and have a maximum diameter that essentially corresponds to the diameter of the cylindrical rod outside the at least one bending area, wherein two adjacent support segments are connected by a flexible section.

2. The method for producing a bent tubular shaft according to claim 1, wherein before the step of bending the tubular shaft functional elements are attached to the distal ends of the hollow shaft component and the actuating rod.

3. The method for producing a bent tubular shaft according to claim 1, wherein providing the at least one bending area of the actuating rod with a friction-reducing layer comprises:
   pulling a shrink tubing over the at least one bending area of the actuating rod; and shrinking the shrink tubing at the at least one bending area of the actuating rod.

4. The method for producing a bent tubular shaft for a tubular shaft instrument according to claim 1, wherein the at least one bending area of the actuating rod does not extend up to one of the two axial ends thereof.

\* \* \* \* \*